(12) United States Patent
Abraham et al.

(10) Patent No.: US 12,029,684 B2
(45) Date of Patent: Jul. 9, 2024

(54) ADJUSTING LASER PULSES TO COMPENSATE FOR INTERFERING OBJECTS

(71) Applicant: Alcon Inc., Fribourg (CH)

(72) Inventors: Mario Abraham, Burgthann (DE); Michael Wittnebel, Hirschaid (DE)

(73) Assignee: Alcon Inc., Fribourg (CH)

( * ) Notice: Subject to any disclaimer, the term of this patent is extended or adjusted under 35 U.S.C. 154(b) by 232 days.

(21) Appl. No.: 17/643,449

(22) Filed: Dec. 9, 2021

(65) Prior Publication Data

US 2022/0183881 A1 Jun. 16, 2022

Related U.S. Application Data

(60) Provisional application No. 63/126,278, filed on Dec. 16, 2020.

(51) Int. Cl.
| | |
|---|---|
| *A61F 9/008* | (2006.01) |
| *A61B 17/00* | (2006.01) |
| *A61B 18/00* | (2006.01) |
| *A61B 90/00* | (2016.01) |
| *G16H 20/40* | (2018.01) |

(52) U.S. Cl.
CPC ............ *A61F 9/008* (2013.01); *A61B 90/361* (2016.02); *G16H 20/40* (2018.01); *A61B 2017/00181* (2013.01); *A61B 2018/00791* (2013.01); *A61F 2009/00844* (2013.01)

(58) Field of Classification Search
CPC ............ A61F 9/008; A61F 2009/00844; A61F 9/00825; A61F 9/0084; A61B 90/361; A61B 2017/00181; A61B 2018/00791; G16H 20/40
See application file for complete search history.

(56) References Cited

U.S. PATENT DOCUMENTS

| | | | |
|---|---|---|---|
| 2009/0149841 A1 | 6/2009 | Kurtz | |
| 2009/0177189 A1 | 7/2009 | Raksi | |
| 2013/0158531 A1* | 6/2013 | Goldshleger | ....... A61F 9/00825 606/6 |
| 2018/0207031 A1 | 7/2018 | Woodley et al. | |
| 2018/0303667 A1 | 10/2018 | Peyman | |
| 2019/0385308 A1* | 12/2019 | Kandlikar | ................. G06T 7/30 |
| 2020/0375666 A1* | 12/2020 | Murphy | ................. A61B 34/20 |

FOREIGN PATENT DOCUMENTS

WO 2018021780 A1 2/2018

* cited by examiner

*Primary Examiner* — Brian T Gedeon
*Assistant Examiner* — Joshua Andrew Schum-Houck

(57) ABSTRACT

In certain embodiments, an ophthalmic surgical system for performing a surgical procedure on an eye comprises a laser device, a camera, and a computer. The laser device comprises a laser source and a scanner. The laser source generates a laser beam comprising pulses, and the scanner directs the pulses towards tissue of the eye according to a laser focal spot pattern. The camera captures surgical images of the eye. The computer instructs the laser device to direct the pulses towards the eye according to the laser focal spot pattern, accesses and monitor the surgical images of the eye, identifies an interfering object from the surgical images of the eye, and modifies the control of the pulses to compensate for the interfering object.

21 Claims, 7 Drawing Sheets

ADJUSTING LASER PULSES TO COMPENSATE FOR INTERFERING OBJECTS

TECHNICAL FIELD

The present disclosure relates generally to ophthalmic surgical systems and methods, and more particularly to adjusting laser pulses to compensate for interfering objects.

BACKGROUND

Laser ablation removes material from a surface by irradiating it with a laser beam. In ophthalmic surgery, an ablation procedure typically uses an excimer laser to reshape the cornea to change its refractive properties. During the procedure, the laser beam is directed towards the cornea according to an ablation profile, which indicates the volume of tissue to be removed at particular positions of the cornea. The beam forces the molecules to detach from each other, and material is removed to yield a desired corneal shape.

The laser beam may be focused according to a focal spot pattern determined from the ablation profile. Given the volume of tissue ablated per pulse, the number of pulses to be directed at a particular position can be calculated from the volume of tissue to be removed according to the ablation profile. To accurately yield the desired corneal shape, the number of pulses defined by the focal spot pattern should reach the tissue. In certain situations, however, pulses may be blocked by an interfering object.

BRIEF SUMMARY

In certain embodiments, an ophthalmic surgical system for performing a surgical procedure on an eye comprises a laser device, a camera, and a computer. The laser device comprises a laser source and a scanner. The laser source generates a laser beam comprising pulses, and the scanner directs the pulses towards tissue of the eye according to a laser focal spot pattern. The camera captures surgical images of the eye. The computer instructs the laser device to direct the pulses towards the eye according to the laser focal spot pattern, accesses and monitor the surgical images of the eye, identifies an interfering object from the surgical images of the eye, and modifies the control of the pulses to compensate for the interfering object.

Embodiments may include none, one, some, or all of the following features: The computer identifies the interfering object from the surgical images of the eye by: accessing one or more descriptions of possible interfering objects, each description comprising a geometric shape corresponding to a possible interfering object; detecting a geometric shape in at least one surgical image of the eye; and identifying the possible interfering object corresponding to the detected geometric shape as the interfering object. The computer identifies the interfering object from the surgical images of the eye by: accessing one or more descriptions of possible interfering objects, each description comprising a representative image corresponding to a possible interfering object; detecting an object in at least one surgical image of the eye that matches a representative image; and identifying the possible interfering object corresponding to the detected object as the interfering object. The computer identifies the interfering object from the surgical images of the eye by: accessing a pre-treatment image of the eye; comparing the pre-treatment image of the eye with at least one surgical image of the eye to determine a difference between the pre-treatment image and the surgical image; and identifying the difference as the interfering object. The surgical image indicates the temperature of objects of the image. The computer identifies the interfering object from the surgical images of the eye by: detecting an object of the image with a temperature that deviates from the temperature of the tissue of the eye; and identifying the detected object as the interfering object. The surgical image indicates distances from the camera for objects of the image. The computer identifies the interfering object from the surgical images of the eye by: detecting an object of the image with a distance that deviates from the distance of the eye; and identifying the detected object as the interfering object. The computer modifies the control of the pulses to compensate for the interfering object by: determining pulses that are blocked by the interfering object; and suspending emission of pulses that are blocked by the interfering object. The computer may emit the suspended pulses: when the interfering object is no longer blocking the pulses, toward the end of the surgical procedure when the interfering object is no longer blocking the pulses, in response to detecting the interfering object is no longer blocking the pulses, and/or when a predicted path indicates the interfering object is no longer blocking the at least one pulse. The computer may generate a notification that the interfering object is blocking the pulses. The interfering object comprises at least one of a surgical instrument, a medical lab tool, a part of the ophthalmic surgical system, a part of a user's body, a part of the patient's body, a living being, or a surgical product.

In certain embodiments, a method for performing a surgical procedure on an eye, comprises: generating, by a laser source of a laser device, a laser beam comprising pulses; directing, by a scanner of a laser device, the pulses towards tissue of the eye according to a laser focal spot pattern; capturing, by a camera, surgical images of the eye; instructing, by a computer, the laser device to direct the pulses towards the eye according to the laser focal spot pattern; accessing and monitoring, by the computer, the surgical images of the eye; identifying, by the computer, an interfering object from the surgical images of the eye; and modifying, by the computer, the control of the pulses to compensate for the interfering object.

Embodiments may include none, one, some, or all of the following features: Identifying the interfering object from the surgical images of the eye comprises: accessing one or more descriptions of possible interfering objects, each description comprising a geometric shape corresponding to a possible interfering object; detecting a geometric shape in at least one surgical image of the eye; and identifying the possible interfering object corresponding to the detected geometric shape as the interfering object. Identifying the interfering object from the surgical images of the eye comprises: accessing one or more descriptions of possible interfering objects, each description comprising a representative image corresponding to a possible interfering object; detecting an object in at least one surgical image of the eye that matches a representative image; and identifying the possible interfering object corresponding to the detected object as the interfering object. Identifying the interfering object from the surgical images of the eye comprises: accessing a pre-treatment image of the eye; comparing the pre-treatment image of the eye with at least one surgical image of the eye to determine a difference between the pre-treatment image and the surgical image; and identifying the difference as the interfering object. The surgical image indicates a temperature of objects of the image. Identifying the interfering object from the surgical images of the eye comprises: detecting an object of the image with a temperature that deviates from the temperature of the tissue of the eye; and identifying the detected object as the interfering object. The surgical image indicates distances from the camera for objects of the image. Identifying the interfering object from the surgical images of the eye comprises: detecting an object of the image with a distance that deviates from the distance of the eye; and identifying the detected object as the interfering object. Modifying the control of the pulses to compensate for the interfering object comprises: determining pulses that are blocked by the interfering object; and suspending emission of pulses that are blocked by the interfering object.

In certain embodiments, an ophthalmic surgical system for performing a surgical procedure on an eye comprises a laser device, a camera, and a computer. The laser device comprises a laser source and a scanner. The laser source generates a laser beam comprising pulses, and the scanner directs the pulses towards tissue of the eye according to a laser focal spot pattern. The camera captures surgical images of the eye. The computer instructs the laser device to direct the pulses towards the eye according to the laser focal spot pattern, and accesses and monitors the surgical images of the eye. The computer identifies the interfering object from the surgical images of the eye by performing at least one of the following: accessing one or more descriptions of possible interfering objects, each description comprising a geometric shape corresponding to a possible interfering object, detecting a geometric shape in at least one surgical image of the eye, and identifying the possible interfering object corresponding to the detected geometric shape as the interfering object; accessing one or more descriptions of possible interfering objects, each description comprising a representative image corresponding to a possible interfering object, detecting an object in at least one surgical image of the eye that matches a representative image, and identifying the possible interfering object corresponding to the detected object as the interfering object; accessing a pre-treatment image of the eye, comparing the pre-treatment image of the eye with at least one surgical image of the eye to determine a difference between the pre-treatment image and the surgical image, and identifying the difference as the interfering object; if the surgical image indicates a temperature of objects of the image, identify the interfering object by detecting an object of the image with a temperature that deviates from the temperature of the tissue of the eye, and identifying the detected object as the interfering object; and if the surgical image indicates distances from the camera for objects of the image, identify the interfering object by detecting an object of the image with a distance that deviates from the distance of the eye, and identifying the detected object as the interfering object. The computer modifies the control of the pulses to compensate for the interfering object by: predicting a path of the interfering object; determining pulses that are blocked by the interfering object; generating a notification that the interfering object is blocking the pulses; suspending emission of pulses that are blocked by the interfering object; and emitting the suspended pulses when the interfering object is no longer blocking the pulses, toward the end of the surgical procedure when the interfering object is no longer blocking the pulses, in response to detecting the interfering object is no longer blocking the pulses, or when the predicted path indicates the interfering object is no longer blocking the at least one pulse. The interfering object comprises at least one of a surgical instrument, a medical lab tool, a part of the ophthalmic surgical system, a part of a user's body, a part of the patient's body, a living being, or a surgical product.

DESCRIPTION OF EXAMPLE EMBODIMENTS

Figure 1:
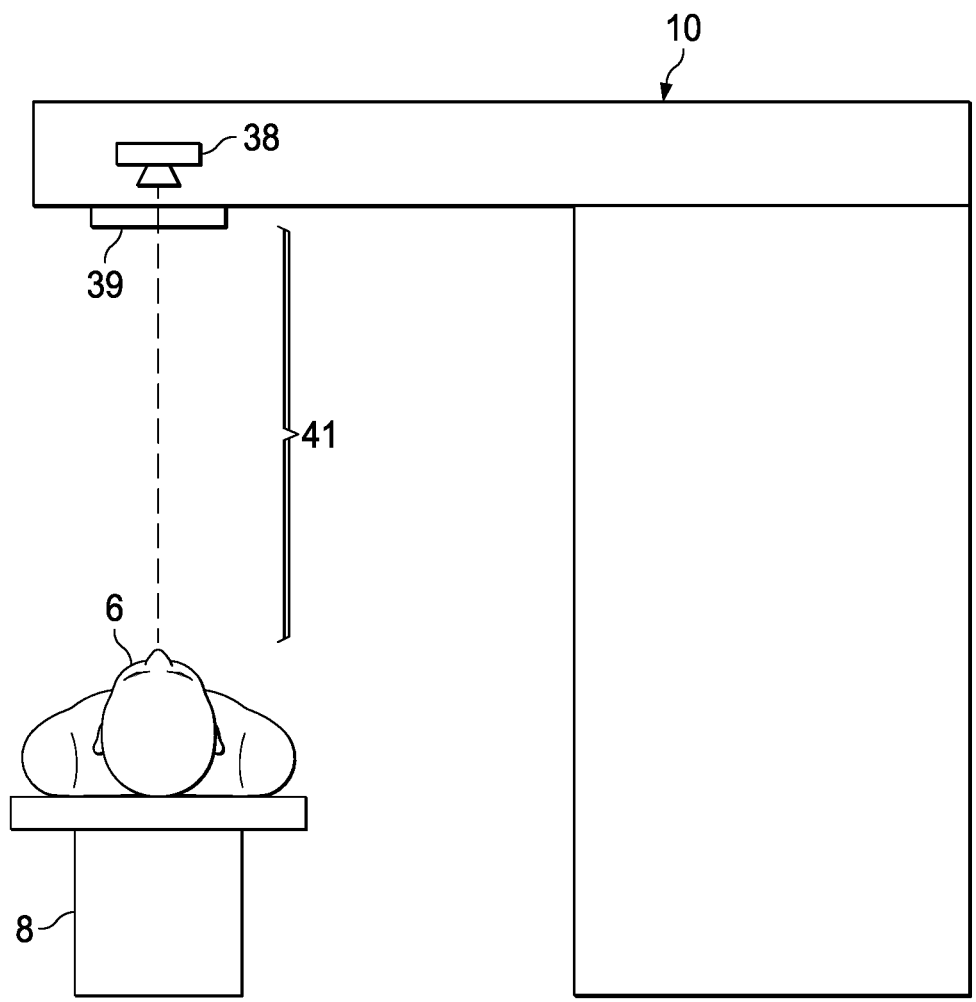
FIGS. 1 and 2 illustrate an example of an ophthalmic laser ablation system that ablates the corneal tissue of an eye of a patient to perform a surgical procedure, according to certain embodiments.

Referring now to the description and drawings, example embodiments of the disclosed apparatuses, systems, and methods are shown in detail. The description and drawings are not intended to be exhaustive or otherwise limit the claims to the specific embodiments shown in the drawings and disclosed in the description. Although the drawings represent possible embodiments, the drawings are not necessarily to scale and certain features may be simplified, exaggerated, removed, or partially sectioned to better illustrate the embodiments.

In certain embodiments, the systems and methods may identify an interfering object that blocks laser pulses directed towards an eye during a surgical procedure. An interfering object may be identified by, e.g.: detecting a geometric shape corresponding to an interfering object; detecting an object that matches a representative image of an interfering object; detecting an object that was not present in pre-treatment images; detecting an object that has a temperature that deviates from the temperature of the eye; and/or detecting an object at a distance between the laser device and the eye. The systems and methods may also modify control of the pulses to compensate for an interfering object. For example, the control may be modified by: emitting the pulses after the interfering object is no longer blocking the pulses; emitting the pulses towards the end of the procedure; and/or sending a notification that an interfering object is blocking the pulses.

Figure 2:
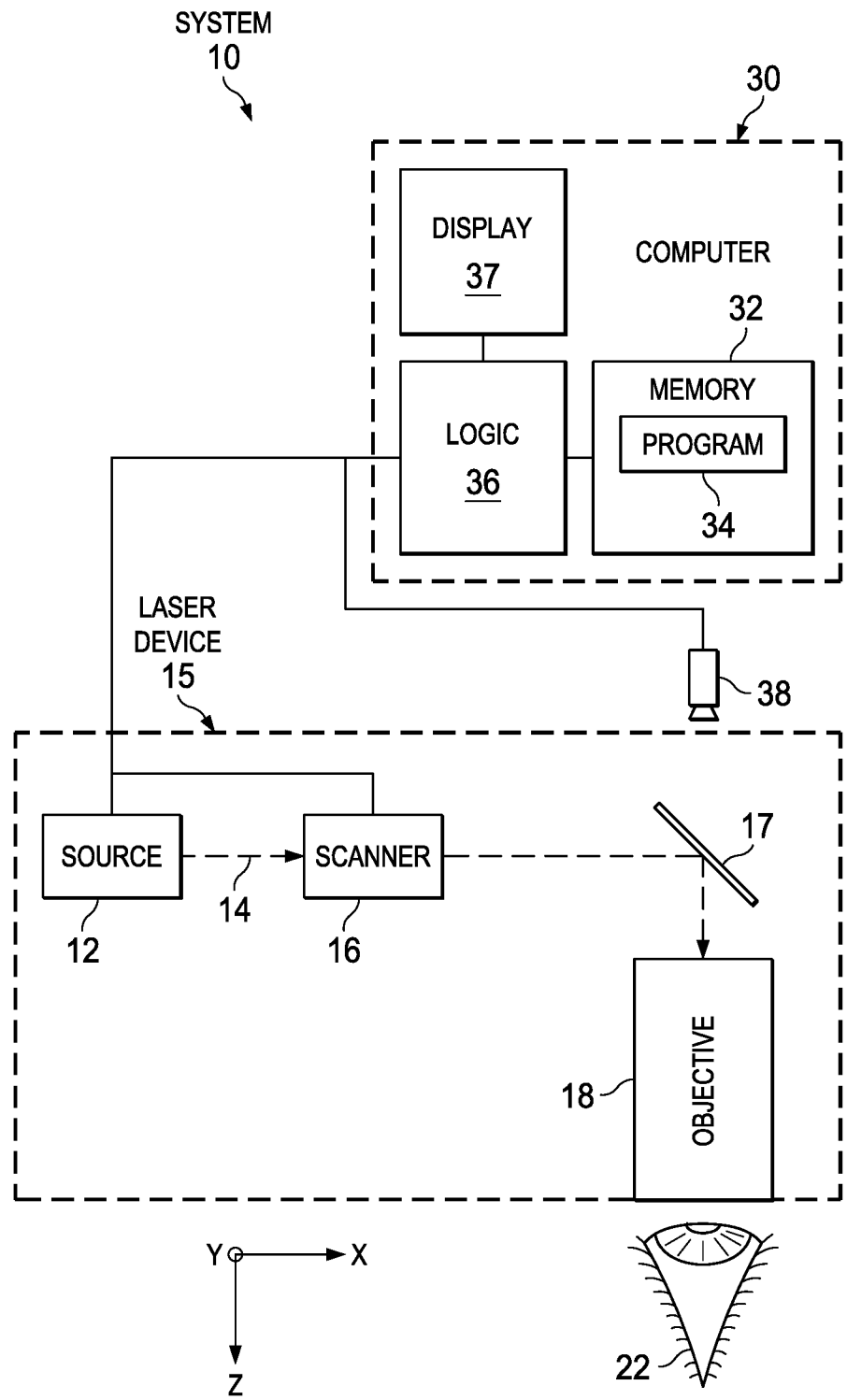

FIGS. 1 and 2 illustrate an example of an ophthalmic laser ablation system 10 that ablates the corneal tissue of an eye of a patient to perform a surgical procedure, according to certain embodiments. System 10 may be used for different types of procedures. For example, laser in-situ keratomileusis (LASIK) involves cutting a flap in the cornea and then using system 10 to ablate the cornea. As another example, in photo refractive keratectomy (PRK), the epithelium is removed, e.g., chemically or mechanically, and then system 10 is used to ablate the cornea.

FIG. 1 shows ophthalmic laser ablation system 10 and a patient 6 lying on a bed 8. In the illustrated example, system 10 includes a camera 38 and a part 39 where a laser beam exits system 10. An interfering object blocks laser pulses from reaching patient 6, and may be located between part 39 and patient 6, e.g., in region 41. Examples of an interfering object include a surgical instrument, a medical lab tool (e.g., tube, pipette, cannula), a part of system 10, a part of the medical personnel's body (e.g., a finger, glove), a living being (e.g., a flying insect) a part of the patient's body (e.g., eyelash), surgical product (e.g., water droplet, ablation mist), or other suitable object that may block laser pulses from reaching patient 6.

In FIG. 2, system 10 includes a laser device 15, camera 38, and a control computer 30, coupled as shown. Laser device 15 includes controllable components, such as a laser source 12, a scanner 16, one or more optical elements 17, and/or a focusing objective 18, coupled as shown. Computer 30 includes logic 36, a memory 32 (which stores a computer program 34), and a display 37, coupled as shown. For ease of explanation, the following xyz-coordinate system is used: The z-direction is defined by the propagation direction of the laser beam, and the xy-plane is orthogonal to the propagation direction. Other suitable xyz-coordinate systems may be used.

Turning to the parts of system 10, laser source 12 generates a laser beam that modifies (e.g., ablates or photodisrupts) tissue of eye 22 according to a laser focal spot pattern. Laser source 12 may be an excimer or femto laser that generates a laser beam with a plurality of laser pulses. A focal spot pattern may define x and y (and perhaps z) coordinates for positions at which laser radiation pulses are to be directed. In certain cases, the focal spot pattern may be determined from an ablation profile, which indicates the volume of tissue to be removed at particular x, y positions of the cornea. Given the volume of tissue ablated per pulse, the number of pulses to be directed at an x, y position can be calculated from the volume of tissue defined by the ablation profile.

Scanner 16 laterally and/or longitudinally directs the focal point of the laser beam according to a laser focal spot pattern. The lateral direction refers to directions orthogonal to the direction of beam propagation, i.e., the x, y directions. Scanner 16 may laterally direct the laser beam in any suitable manner. For example, scanner 16 may include a pair of galvanometrically-actuated scanner mirrors that can be tilted about mutually perpendicular axes. As another example, scanner 16 may include an electro-optical crystal that can electro-optically steer the laser beam.

The longitudinal direction refers to the direction parallel to the laser beam propagation, i.e., the z-direction. Scanner 16 may longitudinally direct the laser beam in any suitable manner. For example, scanner 16 may include a longitudinally adjustable lens, a lens of variable refractive power, or a deformable mirror that can control the z-position of the beam focus. The components of scanner 16 may be arranged in any suitable manner along the beam path, e.g., in the same or different modular units.

One (or more) optical elements 17 direct the laser beam towards focusing objective 18. An optical element 17 can act on (e.g., transmit, reflect, refract, diffract, collimate, condition, shape, focus, modulate, and/or otherwise act on) a laser beam. Examples of optical elements include a lens, prism, mirror, diffractive optical element (DOE), holographic optical element (HOE), and spatial light modulator (SLM). In the example, optical element 17 is a mirror. Focusing objective 18 focuses the focal point of laser beam towards a point of eye 22. In the example, focusing objective 18 is an objective lens, e.g., an f-theta objective.

Camera 38 records surgical images of the eye 22 taken during the surgical procedure. Examples of camera 38 include a video, interferometry, thermal imaging, ultrasound, optical coherence tomography, and eye-tracking camera. Camera 38 delivers image data, which represent recorded images of the eye 22, to computer 30.

Computer 30 controls components of system 10 in accordance with computer program 34. For example, computer 30 controls components (e.g., laser source 12, scanner 16, optical elements 17, and/or focusing objective 18) to focus the laser beam of laser device 15 at eye 22 and to ablate at least a portion of eye 22 according to a laser focal spot pattern. Memory 32 stores information used by computer 30. For example, memory 32 may store images of eye 22 (e.g., surgical and/or pre-treatment images), descriptions of interfering objects 42 (e.g., representative images and/or geometric shapes of the object), and/or other suitable information, and computer 30 may access information from memory 32.

Computer 30 may monitor surgical images and identify an interfering object that blocks laser pulses directed towards an eye. Computer 30 may carry out image processing on the image data to identify interfering objects. In certain embodiments, image processing may be used to identify an interfering object according to a stored description of possible interfering objects, e.g., a geometric shape of and/or a representative image of a possible interfering object, as described in more detail with reference to FIGS. 3 and 4. In other embodiments, image processing may be used to compare pre-treatment images with surgical images to detect an object that was not present in pre-treatment images, indicating an interfering object, as described in more detail with reference to FIG. 5. In other embodiments, image processing may be used to detect an object that has a temperature that deviates from the temperature of the eye, indicating an interfering object, as described in more detail with reference to FIG. 6. In other embodiments, image processing may be used to detect an object at a distance between the laser device and the eye, indicating an interfering object, as described in more detail with reference to FIG. 7.

Computer 30 may identify pulses that are blocked by an interfering object and modify control of the blocked pulses to compensate for the interfering object. In certain embodiments, computer 30 may identify the blocked pulses by determining the location of the interfering object from a surgical image and identifying which pulses are directed to that location according to the focal spot pattern.

In certain embodiments, computer 30 may modify control of the blocked pulses by suspending emission of the blocked pulses and then resolving the issue of the blocked pulses. In certain embodiments, computer 30 may perform one or more of the following to resolve the issue: (1) From the images, detect that the interfering object is no longer at a location that blocks at least some pulses and emit the pulses that are no longer blocked. (2) Emit the pulses towards the end of the procedure, e.g., after the other pulses of the laser focal spot pattern have been emitted. (3) Send a notification that an interfering object is blocking the pulses. In response, a user may move the interfering object to no longer block the pulses. (4) Predict a path of the interfering object from, e.g. the previous path and/or known information about the movement of other objects like the interfering object. Then, emit the pulses when the predicted path indicates they are no longer blocked.

Figure 3:
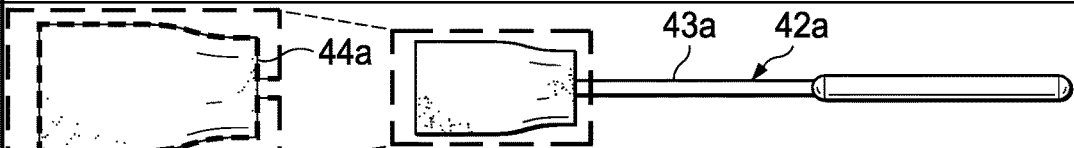
FIG. 3 illustrates a table of examples of possible interfering objects and their corresponding descriptions.

FIG. 3 illustrates a table 40 of examples of possible interfering objects 42 (42a-42h) and their corresponding descriptions. The descriptions may include, e.g., representative images 43 (43a-43h) and/or geometric shapes 44 (44a-44h) of objects 42, and may describe objects 42 in two- or three-dimensions. Memory 32 may store table 40. Representative images 43 may be stored as image data of photos of possible interfering objects 42, and geometric shapes 44 may be stored as a list of attributes, e.g., vectors, that describe possible interfering objects 42. Computer 30 may access table 40 from memory 32 to identify interfering objects 42 in surgical images according to their corresponding representative images 43 and/or geometric shapes 44. Examples of interfering objects 42 (42a-42h) include: surgical sponges 42a-b, LASIK flap elevator 42c, paton 42d, hockey knife 42e, lindstrom 42f, LASIK pick 42g, and LASIK flap forceps 42h.

Figure 4:
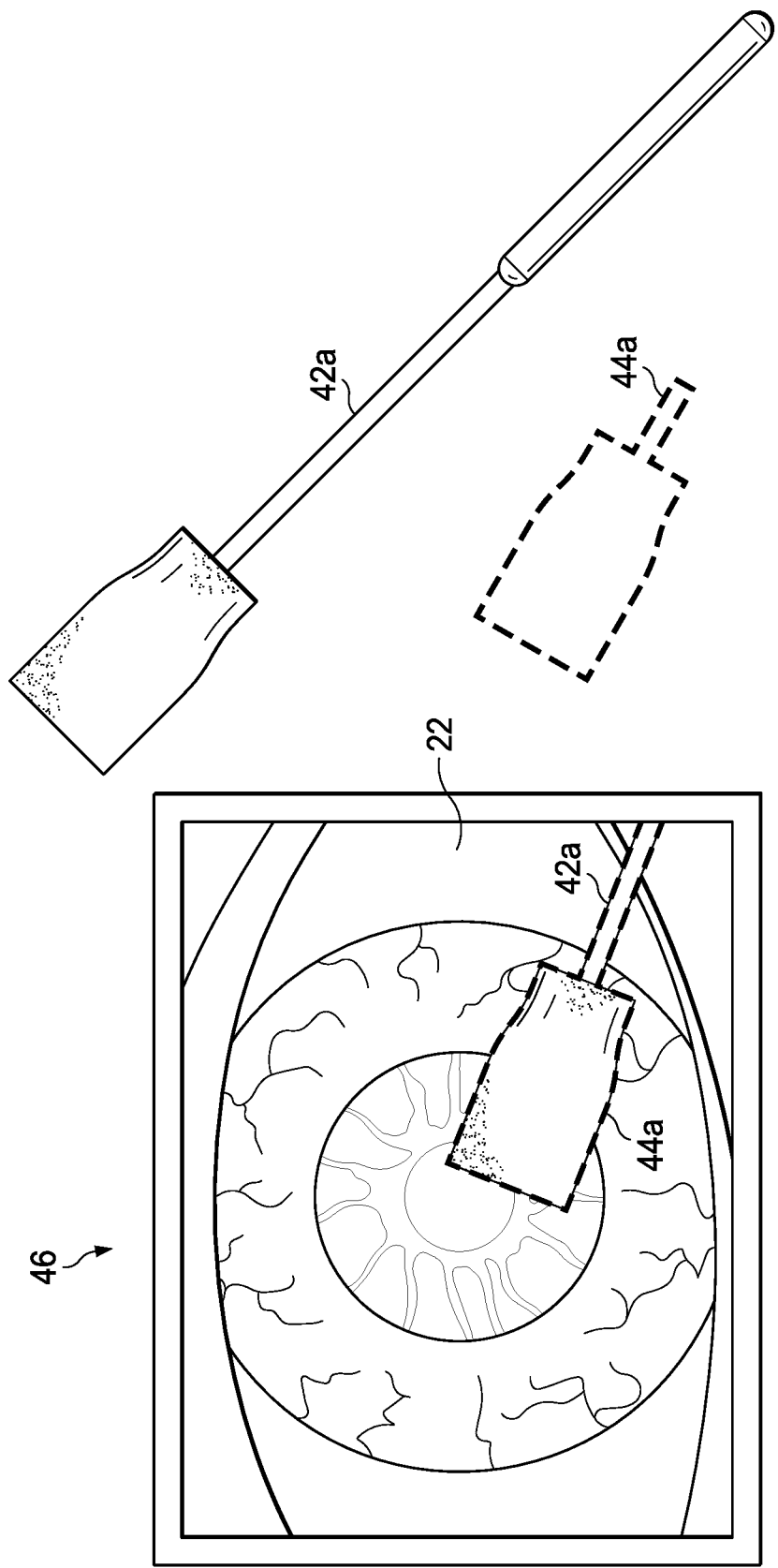
FIG. 4 illustrates an example of a surgical image of eye and an interfering object.

FIG. 4 illustrates an example of a surgical image 46 of eye 22 and an interfering object 42a. In certain embodiments, computer 30 performs image processing on surgical image 26 to identify a geometric shape 44a of image. For example, surgical image 26 is analyzed to detect borders of a region with a color and/or brightness that deviates from the color and/or brightness of eye, and determines if the borders match a geometric shape 44 of table 40. If there is a match, computer 30 may determine interfering object 42a has been identified. In the example, computer identifies interfering object 42a.

In certain embodiments, computer 30 performs image processing on surgical image 26 to identify an object that matches a representative image 43. For example, at least some pixels of surgical image 26 are compared with at least some pixels of representative image 43 to see if surgical image 26 substantially matches with representative image 43. If there is a match, computer 30 may determine interfering object 42a has been identified. In the example, computer identifies interfering object 42a.

Figure 5:
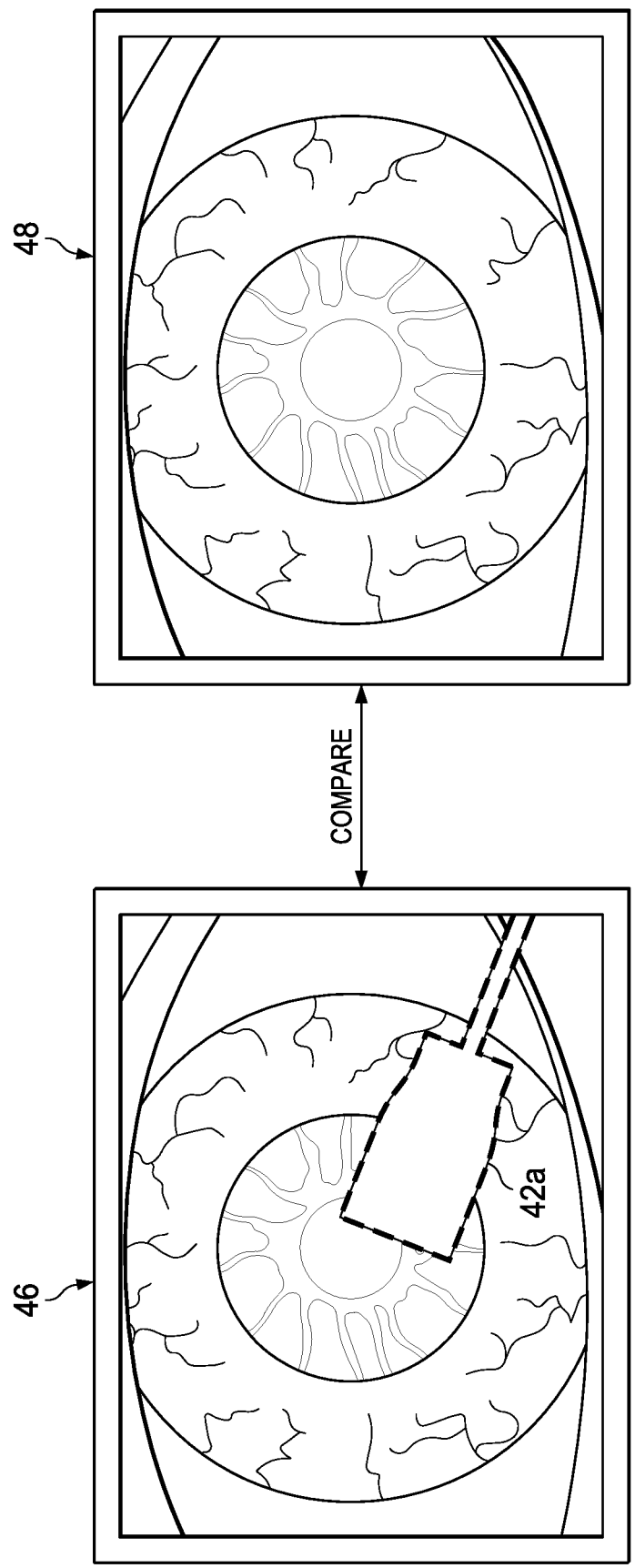
FIG. 5 illustrates an example of a comparison of surgical and pre-treatment images of an eye to identify an interfering object.

FIG. 5 illustrates an example of a comparison of surgical image 46 and pre-treatment image 48 of eye 22 to identify an interfering object 42a. In the example, computer 30 accesses images 46, 48 (from, e.g., memory 32) and performs image processing to compare images 46, 48 to identify differences between images 46, 48. For example, corresponding pixels of images 46, 48 are compared, and differences are recorded. The differences that exceed predefined tolerances correspond to interfering object 42a. A predefined tolerance may be set to distinguish an interfering object from other differences (e.g., image artifacts or differences in eye 22 from image to image), and may have a value in one or more of the following ranges, 2 to 5, 5 to 10, 10 to 20, and/or greater than 20 percent. In the example, computer 30 identifies the difference as interfering object 42a.

Figure 6:
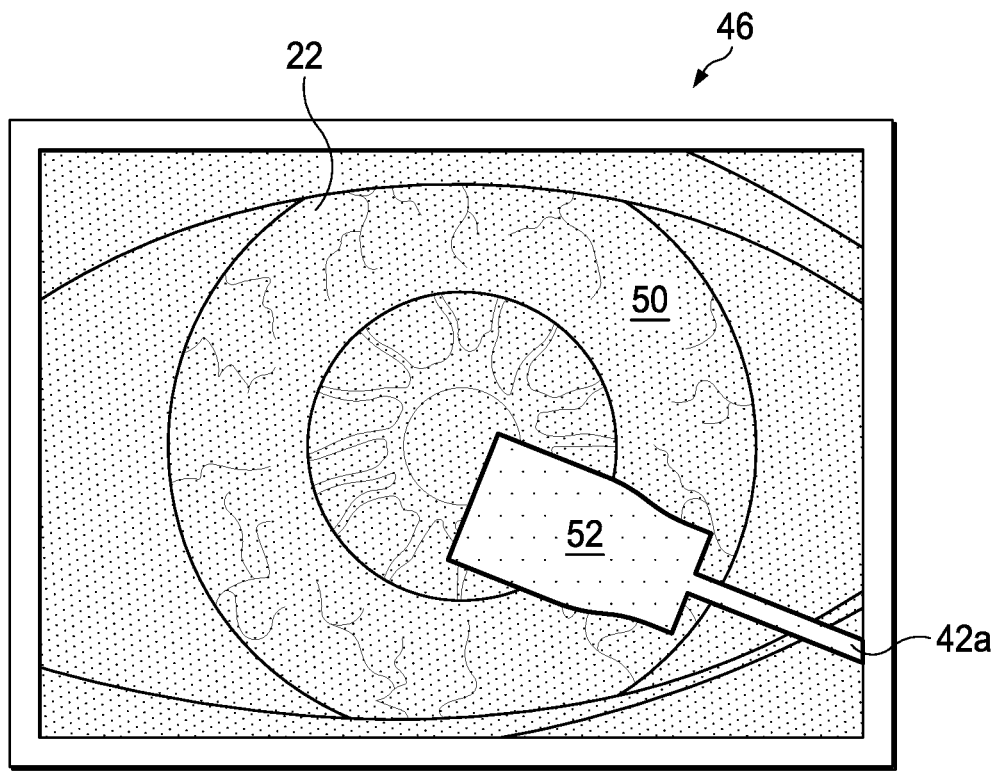
FIG. 6 illustrates an example of a surgical image used to identify an interfering object using the temperature of objects.

FIG. 6 illustrates an example of a surgical image 46 used to identify an interfering object 42a using the temperature of objects in image 46. In the example, surgical image 46 is a thermal image generated by a thermal imaging camera (e.g., infrared camera) that indicates the surface temperature of objects in image 46. Image 46 shows eye 22 with a higher temperature in one color 50 and interfering object 42a of a lower temperature in another color 52. Computer 30 identifies the region in color 52 as interfering object 42a.

Figure 7:
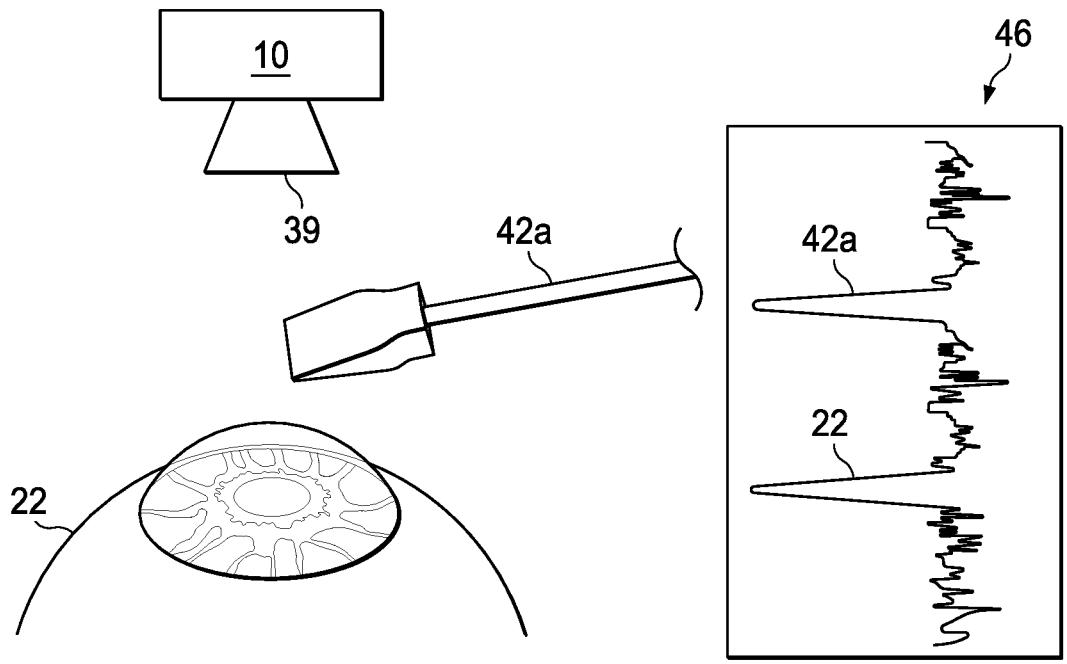
FIG. 7 illustrates an example of a surgical image used to identify an interfering object using the distances of objects.

FIG. 7 illustrates an example of a surgical image 46 used to identify an interfering object 42a using the distances of objects in image 46. In the example, system 10 includes a camera, e.g., an interferometry, OCT, ultrasound, or other camera that generates surgical images that indicate distance from the camera. In the example, an image taken by the camera may comprise distance measurements, e.g., location-based depth scans that have amplitude peaks indicating the location of objects. In certain embodiments, the distance between a part 39 where a laser beam exits system 10 and eye 22 is known, and distances between part 39 and eye 22 indicate an interfering object 42. In the example, computer 30 identifies an object between part 39 and eye 22 as interfering object 42a.

Figure 8:
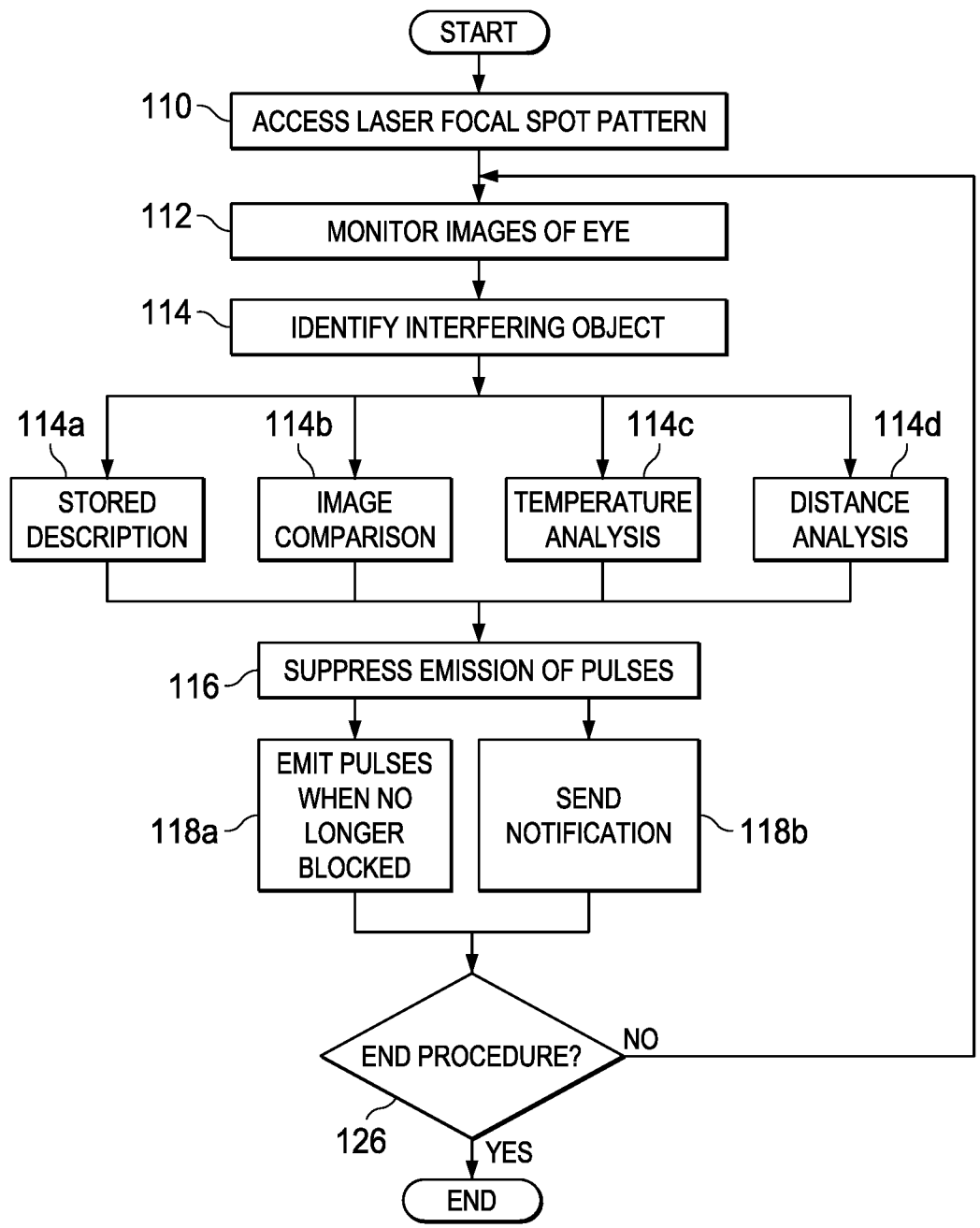
FIG. 8 illustrates an example of a method for identifying and compensating for interfering objects in surgical procedures, which may be performed by the system of FIG. 1, according to certain embodiments.

FIG. 8 illustrates an example of a method for identifying and compensating for interfering objects in surgical procedures, which may be performed by system 10 of FIG. 1, according to certain embodiments. In the embodiments, computer 30 may instruct components of system 10 to perform certain steps. The method starts at step 110, where computer 30 accesses a laser focal spot pattern that indicates the placement of laser pulses for a surgical procedure. Computer 30 monitors images of eye 22 from camera 38 at step 112.

Computer 30 identifies an interfering object 42 at step 114. Interfering object 42 may be identified in any suitable manner, e.g., as described in steps 114a-d. At step 114a, computer 30 identifies an interfering object according to a stored description of possible interfering objects, e.g., a geometric shape of and/or a representative image of a possible interfering object. At step 114b, computer 30 compares pre-treatment images with surgical images to detect an object that was not present in pre-treatment images, indicating an interfering object. At step 114c, computer 30 detects an object that has a temperature that deviates from the temperature of the eye, indicating an interfering object. At step 114c, computer 30 detects an object at a distance between the laser device and the eye, indicating an interfering object.

Computer 30 suspends emission of pulses that are blocked by the interfering object at step 116. Computer 30 may perform one or more additional steps 118a-b to resolve the issue of the blocked pulses. Computer 30 emits the suspended pulses when the interfering object is no longer blocking the pulses at step 118a. For example, computer 30 may emit the suspended pulses toward the end of the surgical procedure when the interfering object is no longer blocking the pulses. As another example, computer 30 may detect that the interfering object is no longer blocking the pulses, and emit the suspended pulses in response to the detection. As yet another example, computer 30 may determine that the interfering object is no longer blocking the pulses according a predicted path of the object, and emit the suspended pulses in response to the determination. Computer 30 generates a notification that the interfering object is blocking the pulses at step 118b. In response, a user may move the interfering object.

The procedure may end at step 126. If the procedure does not end, the method returns to step 112, where computer 30 monitors images of eye 22. If the procedure ends, the method ends.

A component (such as the control computer) of the systems and apparatuses disclosed herein may include an interface, logic, and/or memory, any of which may include computer hardware and/or software. An interface can receive input to the component and/or send output from the component, and is typically used to exchange information between, e.g., software, hardware, peripheral devices, users, and combinations of these. A user interface (e.g., a Graphical User Interface (GUI)) is a type of interface that a user can utilize to interact with a computer. Examples of user interfaces include a display, touchscreen, keyboard, mouse, gesture sensor, microphone, and speakers.

Logic can perform operations of the component. Logic may include one or more electronic devices that process data, e.g., execute instructions to generate output from input. Examples of such an electronic device include a computer, processor, microprocessor (e.g., a Central Processing Unit (CPU)), and computer chip. Logic may include computer software that encodes instructions capable of being executed by the electronic device to perform operations. Examples of computer software include a computer program, application, and operating system.

A memory can store information and may comprise tangible, computer-readable, and/or computer-executable storage medium. Examples of memory include computer memory (e.g., Random Access Memory (RAM) or Read Only Memory (ROM)), mass storage media (e.g., a hard disk), removable storage media (e.g., a Compact Disk (CD) or Digital Video or Versatile Disk (DVD)), database, network storage (e.g., a server), and/or other computer-readable media. Particular embodiments may be directed to memory encoded with computer software.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, or the operations of the systems and apparatuses may be performed by more, fewer, or other components, as apparent to those skilled in the art. As another example, modifications may be made to the methods disclosed herein. The methods may include more, fewer, or other steps, and the steps may be performed in any suitable order, as apparent to those skilled in the art.

To aid the Patent Office and readers in interpreting the claims, Applicants note that they do not intend any of the claims or claim elements to invoke 35 U.S.C. § 112(f), unless the words "means for" or "step for" are explicitly used in the particular claim. Use of any other term (e.g., "mechanism," "module," "device," "unit," "component," "element," "member," "apparatus," "machine," "system," "processor," or "controller") within a claim is understood by the applicants to refer to structures known to those skilled in the relevant art and is not intended to invoke 35 U.S.C. § 112(f).

What is claimed:

1. An ophthalmic surgical system for performing a surgical procedure on an eye, the system comprising:
a laser device comprising:
a laser source configured to generate a laser beam comprising a plurality of pulses; and
a scanner configured to direct the pulses towards tissue of the eye according to a laser focal spot pattern;
a camera configured to capture a plurality of surgical images of the eye; and
a computer configured to:
instruct the laser device to direct the pulses towards the eye according to the laser focal spot pattern;
access and monitor the plurality of surgical images of the eye;
identify an interfering object comprising a surgical instrument from the surgical images of the eye; and
modify control of the pulses to compensate for the interfering object.

2. The ophthalmic surgical system of claim 1, wherein the computer is configured to identify the interfering object from the surgical images of the eye by:
accessing one or more descriptions of possible interfering objects, each description comprising a geometric shape corresponding to a possible interfering object;
detecting a geometric shape in at least one surgical image of the eye; and
identifying the possible interfering object corresponding to the detected geometric shape as the interfering object.

3. The ophthalmic surgical system of claim 1, wherein the computer is configured to identify the interfering object from the surgical images of the eye by:
accessing one or more descriptions of possible interfering objects, each description comprising a representative image corresponding to a possible interfering object;
detecting an object in at least one surgical image of the eye that matches a representative image; and
identifying the possible interfering object corresponding to the detected object as the interfering object.

4. The ophthalmic surgical system of claim 1, wherein the computer is configured to identify the interfering object from the surgical images of the eye by:
accessing a pre-treatment image of the eye;
comparing the pre-treatment image of the eye with at least one surgical image of the eye to determine a difference between the pre-treatment image and the surgical image; and
identifying the difference as the interfering object.

5. The ophthalmic surgical system of claim 1, wherein:
the surgical image indicates a temperature of a plurality of objects of the image; and
the computer is configured to identify the interfering object from the surgical images of the eye by:
detecting an object of the image with a temperature that deviates from the temperature of the tissue of the eye; and
identifying the detected object as the interfering object.

6. The ophthalmic surgical system of claim 1, wherein:
the surgical image indicates a plurality of distances from the camera for a plurality of objects of the image; and
the computer is configured to identify the interfering object from the surgical images of the eye by:
the eye; and
detecting an object of the image with a distance that deviates from the distance of identifying the detected object as the interfering object.

7. The ophthalmic surgical system of claim 1, wherein the computer is configured to modify the control of the pulses to compensate for the interfering object by:
determining pulses that are blocked by the interfering object; and
suspending emission of pulses that are blocked by the interfering object.

8. The ophthalmic surgical system of claim 7, wherein the computer is configured to modify the control of the pulses to compensate for the interfering object by:
emitting the suspended pulses when the interfering object is no longer blocking the pulses.

9. The ophthalmic surgical system of claim 7, wherein the computer is configured to modify the control of the pulses to compensate for the interfering object by:

emitting the suspended pulses toward an end of the surgical procedure when the interfering object is no longer blocking the pulses.

10. The ophthalmic surgical system of claim 7, wherein the computer is configured to modify the control of the pulses to compensate for the interfering object by:
   detecting that the interfering object is no longer blocking the pulses; and
   emitting the suspended pulses in response to detecting the interfering object is no longer blocking the pulses.

11. The ophthalmic surgical system of claim 7, wherein the computer is configured to modify the control of the pulses to compensate for the interfering object by:
   generating a notification that the interfering object is blocking the pulses.

12. The ophthalmic surgical system of claim 7, wherein the computer is configured to modify the control of the pulses to compensate for the interfering object by:
   predicting a path of the interfering object; and
   emitting at least one of the suspended pulses when the predicted path indicates the interfering object is no longer blocking the pulses.

13. The ophthalmic surgical system of claim 1, wherein:
   the computer is configured to identify a next interfering object from the surgical images of the eye; and
   the next interfering object comprises at least one of a next surgical instrument, a medical lab tool, a part of the ophthalmic surgical system, a part of a user's body, a part of a patient's body, a living being, or a surgical product.

14. A method for performing a surgical procedure on an eye, comprising:
   generating, by a laser source of a laser device, a laser beam comprising a plurality of pulses;
   directing, by a scanner of a laser device, the pulses towards tissue of the eye according to a laser focal spot pattern;
   capturing, by a camera, a plurality of surgical images of the eye;
   instructing, by a computer, the laser device to direct the pulses towards the eye according to the laser focal spot pattern;
   accessing and monitoring, by the computer, the plurality of surgical images of the eye;
   identifying, by the computer, an interfering object comprising a surgical instrument from the surgical images of the eye; and
   modifying, by the computer, control of the pulses to compensate for the interfering object.

15. The method of claim 14, wherein identifying the interfering object from the surgical images of the eye comprises:
   accessing one or more descriptions of possible interfering objects, each description comprising a geometric shape corresponding to a possible interfering object;
   detecting a geometric shape in at least one surgical image of the eye; and
   identifying the possible interfering object corresponding to the detected geometric shape as the interfering object.

16. The method of claim 14, wherein identifying the interfering object from the surgical images of the eye comprises:
   accessing one or more descriptions of possible interfering objects, each description comprising a representative image corresponding to a possible interfering object;
   detecting an object in at least one surgical image of the eye that matches a representative image; and
   identifying the possible interfering object corresponding to the detected object as the interfering object.

17. The method of claim 14, wherein identifying the interfering object from the surgical images of the eye comprises:
   accessing a pre-treatment image of the eye;
   comparing the pre-treatment image of the eye with at least one surgical image of the eye to determine a difference between the pre-treatment image and the surgical image; and
   identifying the difference as the interfering object.

18. The method of claim 14, wherein:
   the surgical image indicates a temperature of a plurality of objects of the image; and
   identifying the interfering object from the surgical images of the eye comprises:
      detecting an object of the image with a temperature that deviates from the temperature of the tissue of the eye; and
      identifying the detected object as the interfering object.

19. The method of claim 14, wherein:
   the surgical image indicates a plurality of distances from the camera for a plurality of objects of the image; and
   identifying the interfering object from the surgical images of the eye comprises:
      detecting an object of the image with a distance that deviates from the distance of the eye; and
      identifying the detected object as the interfering object.

20. The method of claim 14, wherein modifying the control of the pulses to compensate for the interfering object comprises:
   determining pulses that are blocked by the interfering object; and
   suspending emission of pulses that are blocked by the interfering object.

21. An ophthalmic surgical system for performing a surgical procedure on an eye, the system comprising:
   a laser device comprising:
      a laser source configured to generate a laser beam comprising a plurality of pulses; and
      a scanner configured to direct the pulses towards tissue of the eye according to a laser focal spot pattern;
   a camera configured to capture a plurality of surgical images of the eye; and
   a computer configured to:
      instruct the laser device to direct the pulses towards the eye according to the laser focal spot pattern;
      access and monitor the plurality of surgical images of the eye;
      identify an interfering object from the surgical images of the eye by performing at least one of the following:
         accessing one or more descriptions of possible interfering objects, each description comprising a geometric shape corresponding to a possible interfering object, detecting a geometric shape in at least one surgical image of the eye, and identifying the possible interfering object corresponding to the detected geometric shape as the interfering object;
         accessing one or more descriptions of possible interfering objects, each description comprising a representative image corresponding to a possible interfering object, detecting an object in at least one surgical image of the eye that matches a representative image, and identifying the possible interfering object corresponding to the detected object as the interfering object;

accessing a pre-treatment image of the eye, comparing the pre-treatment image of the eye with at least one surgical image of the eye to determine a difference between the pre-treatment image and the surgical image, and identifying the difference as the interfering object;

if the surgical image indicates a temperature of a plurality of objects of the image, identify the interfering object by detecting an object of the image with a temperature that deviates from the temperature of the tissue of the eye, and identifying the detected object as the interfering object; and if the surgical image indicates a plurality of distances from the camera for a plurality of objects of the image, identify the interfering object by detecting an object of the image with a distance that deviates from the distance of the eye, and identifying the detected object as the interfering object; and modify control of the pulses to compensate for the interfering object by:

predicting a path of the interfering object;

determining pulses that are blocked by the interfering object;

generating a notification that the interfering object is blocking the pulses;

suspending emission of pulses that are blocked by the interfering object; and emitting the suspended pulses when the interfering object is no longer blocking the pulses, toward an end of the surgical procedure when the interfering object is no longer blocking the pulses, in response to detecting the interfering object is no longer blocking the pulses, or when the predicted path indicates the interfering object is no longer blocking the pulses, wherein the interfering object comprises a surgical instrument.

\* \* \* \* \*